(12) United States Patent
Kodama

(10) Patent No.: US 10,799,093 B2
(45) Date of Patent: Oct. 13, 2020

(54) ENDOSCOPE HAVING ATTACHABLE/DETACHABLE RAISE BASE

(71) Applicant: OLYMPUS CORPORATION, Tokyo (JP)

(72) Inventor: Hiroshi Kodama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 347 days.

(21) Appl. No.: 15/883,434

(22) Filed: Jan. 30, 2018

(65) Prior Publication Data

US 2018/0153377 A1 Jun. 7, 2018

Related U.S. Application Data

(63) Continuation of application No. PCT/JP2016/071324, filed on Jul. 20, 2016.

(30) Foreign Application Priority Data

Jul. 30, 2015 (JP) ................. 2015-151286

(51) Int. Cl.
*A61B 1/018* (2006.01)
*A61B 1/005* (2006.01)
(Continued)

(52) U.S. Cl.
CPC ...... *A61B 1/00098* (2013.01); *A61B 1/00101* (2013.01); *G02B 23/24* (2013.01);
(Continued)

(58) Field of Classification Search
CPC ............ A61B 1/00098; A61B 1/00101; A61B 1/00121; A61B 1/00133; A61B 1/00137;
(Continued)

(56) References Cited

U.S. PATENT DOCUMENTS 5,569,157 A * 10/1996 Nakazawa ........... A61B 1/0008
600/104
5,674,181 A 10/1997 Iida
2005/0222493 A1 10/2005 Kohno

FOREIGN PATENT DOCUMENTS

DE 296 02 860 U1 5/1996
EP 0 066 120 A2 12/1982
(Continued)

OTHER PUBLICATIONS

Extended Supplementary European Search Report dated Apr. 17, 2019 in European Patent Application No. 16 83 0406.1.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope adapted to insert a treatment tool includes: an opening portion from which the treatment tool protrudes, the opening portion being provided on a distal end of the endoscope; a rotary shaft rotatably mounted in the opening portion, a direction of a shaft center being perpendicular to a longitudinal direction of the endoscope; and a raise base that is attachable to the rotary shaft and detachable from the rotary shaft in a predetermined attaching/detaching direction through the opening portion and is capable of rising around the rotary shaft while being attached to the rotary shaft.

10 Claims, 8 Drawing Sheets

(51) Int. Cl.
  *A61B 1/00* (2006.01)
  *G02B 23/24* (2006.01)
  *A61B 8/12* (2006.01)

(52) U.S. Cl.
  CPC ........... *A61B 1/005* (2013.01); *A61B 1/00121* (2013.01); *A61B 1/00133* (2013.01); *A61B 1/00137* (2013.01); *A61B 1/018* (2013.01); *A61B 8/12* (2013.01)

(58) Field of Classification Search
  CPC ........... A61B 1/005; A61B 1/018; A61B 8/12; G02B 23/24
  See application file for complete search history.

(56) References Cited

FOREIGN PATENT DOCUMENTS

| | | |
|---|---|---|
| JP | H06014873 A | 1/1994 |
| JP | H07000303 U | 1/1995 |
| JP | H08243076 A | 9/1996 |
| JP | H11004804 A | 1/1999 |
| JP | 2001145597 A | 5/2001 |
| JP | 2001145629 A | 5/2001 |
| JP | 2005287593 A | 10/2005 |

OTHER PUBLICATIONS

International Search Report dated Sep. 27, 2016 issued in PCT/JP2016/071324.
Japanese Office Action dated May 15, 2017 issued in JP Patent Application No. 2017-517140.

\* cited by examiner

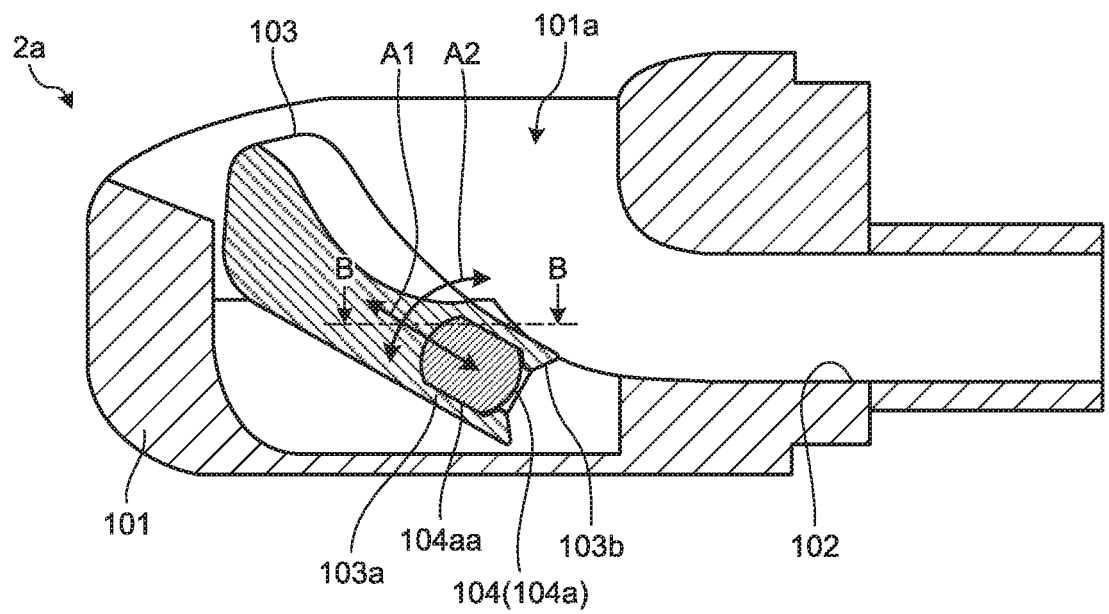
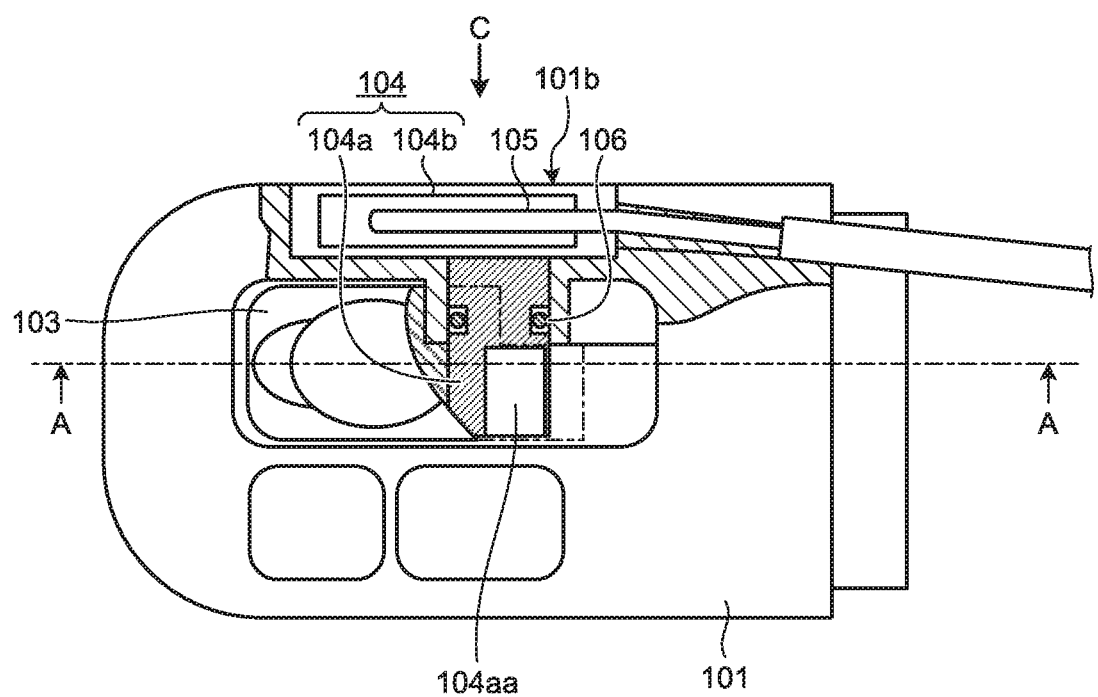

ENDOSCOPE HAVING ATTACHABLE/DETACHABLE RAISE BASE

CROSS REFERENCES TO RELATED APPLICATIONS

This application is a continuation of PCT international application Ser. No. PCT/JP2016/071324, filed on Jul. 20, 2016 which designates the United States, incorporated herein by reference, and which claims the benefit of priority from Japanese Patent Application No. 2015-151286, filed on Jul. 30, 2015, incorporated herein by reference.

BACKGROUND

The present disclosure relates to an endoscope.

Endoscopes, which are inserted into the subject to conduct observations, and the like, on the region to be examined, are known and widely used in medical fields, and the like. Some of the recent endoscopes include a raise base that delivers a treatment tool such as a puncture needle to a diseased site to provide intra-subject treatment. For example, Japanese Laid-open Patent Publication No. 6-14873 discloses a raise base that is rotatably supported on a rotary shaft. According to the technique, a wire connected to the raise base for operation is pulled to the proximal end side so that the raise base is rotated to raise the treatment tool.

SUMMARY

An endoscope according to one aspect of the present disclosure is adapted to insert a treatment tool and includes: an opening portion from which the treatment tool protrudes, the opening portion being provided on a distal end of the endoscope; a rotary shaft rotatably mounted in the opening portion, a direction of a shaft center being perpendicular to a longitudinal direction of the endoscope; and a raise base that is attachable to the rotary shaft and detachable from the rotary shaft in a predetermined attaching/detaching direction through the opening portion and is capable of rising around the rotary shaft while being attached to the rotary shaft.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a schematic cross-sectional view of a distal end portion of the endoscope illustrated in FIG. 1;

FIG. 3 is a schematic diagram that illustrates the top surface and the partial cross-sectional surface of the distal end portion in FIG. 2;

DETAILED DESCRIPTION

Figure 1:
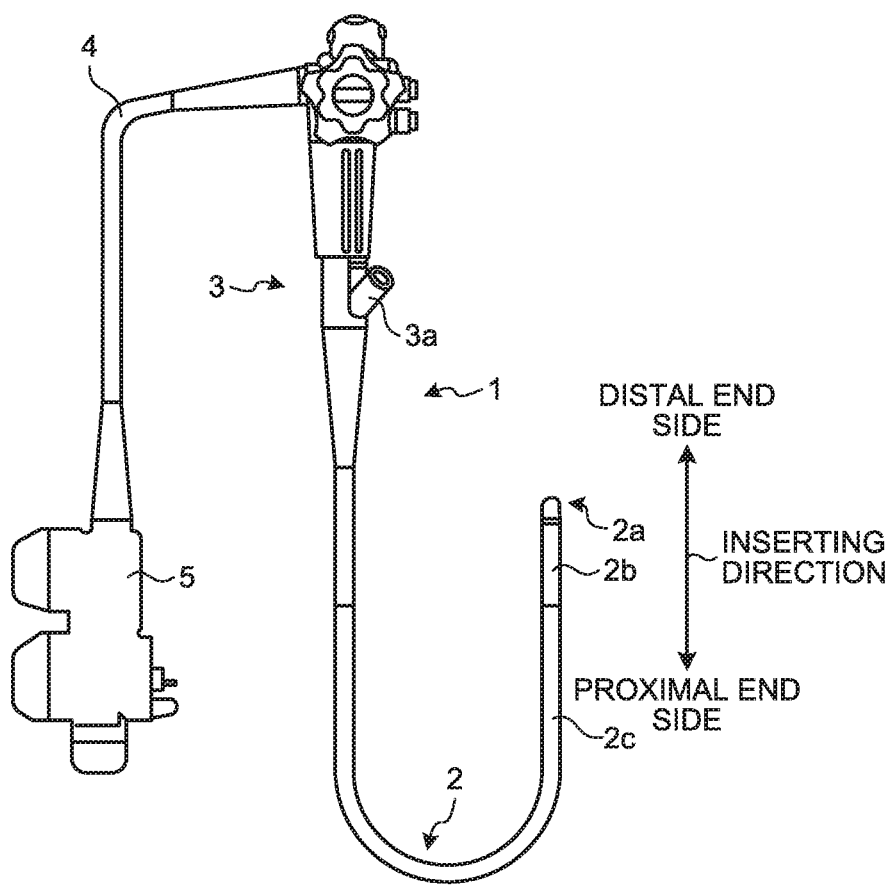
FIG. 1 is a schematic diagram that illustrates a configuration of an endoscope according to a first embodiment.

With reference to drawings, an explanation is given below of an embodiment of an endoscope according to the present disclosure. The present disclosure is not limited to the embodiment. The present disclosure is typically applicable to endoscopes that use a treatment tool such as a puncture needle to provide in-vivo treatment.

Furthermore, in description of the drawings, the identical or corresponding elements are attached with the same reference numeral as appropriate. Moreover, it should be noted that the drawings are schematic and the relation between elements in dimension, the proportion of each element, and the like, are sometimes differ from reality. Each of the drawings sometimes includes parts where the relation in dimension or the proportion is different from each other.

First Embodiment

FIG. 1 is a schematic diagram that illustrates a configuration of an endoscope according to a first embodiment. An endoscope 1 includes an insertion section 2 that has an imaging unit provided on its distal end and that is inserted into the subject; an operating unit 3 that is continuous with the proximal end side of the insertion section 2; a universal code 4 that extends from the side portion of the operating unit 3; a connector section 5 that is continuous with the universal code 4 and is connected to an observation device, which controls the endoscope 1, a light source device, which supplies illumination light to the endoscope 1, or the like. Furthermore, in this specification, as illustrated in FIG. 1, the direction which is the longitudinal direction of the endoscope and in which the insertion section 2 is inserted is "the inserting direction", the distal end side (up in FIG. 1) in the inserting direction is "the distal end side", and the proximal end side (down in FIG. 1) is "the proximal end side".

Starting from the distal end side, the insertion section 2 includes a distal end portion 2a; a curved portion 2b that is configured to be flexibly curved in accordance with an operation of the operating unit 3; and a flexible tube portion 2c that has flexibility. The proximal end of the flexible tube portion 2c is continuous with the distal end side of the operating unit 3. In the distal end portion 2a, a raise base is provided to raise the distal end of a treatment tool as described later.

The operating unit 3 is provided with a treatment-tool insertion opening 3a to insert a treatment tool such as a puncture needle into the subject. A treatment-tool insertion path is provided inside the insertion section 2, and the treatment-tool insertion opening 3a is an insertion opening for the treatment-tool insertion path. Furthermore, the operating unit 3 receives operation to rotate a rotary shaft that is described later.

Figure 4:
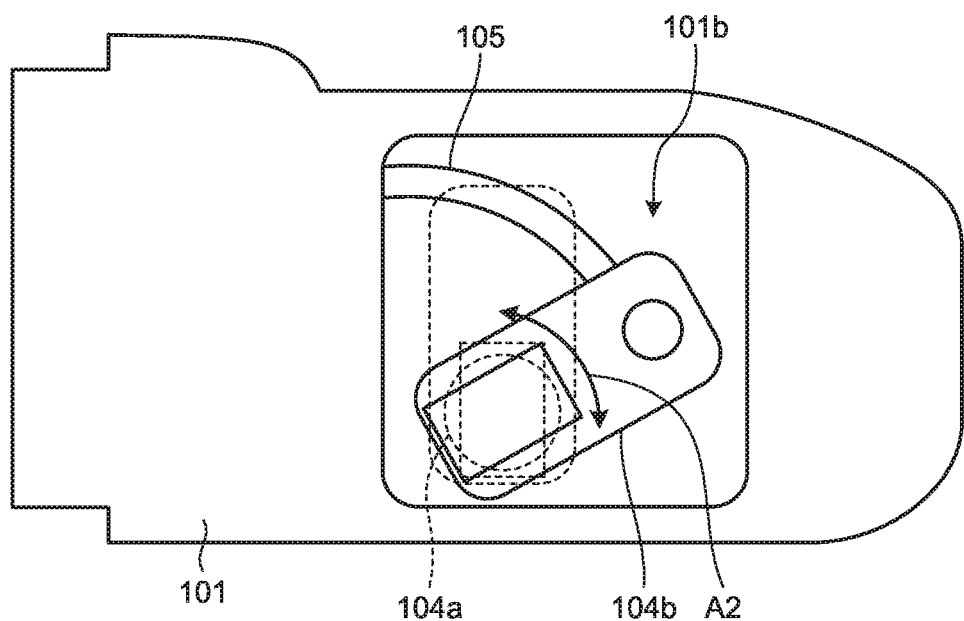
FIG. 4 is a diagram when the distal end portion is viewed in the direction C in FIG. 3.

FIG. 2 is a schematic cross-sectional view of the distal end portion of the endoscope illustrated in FIG. 1. FIG. 3 is a schematic diagram that illustrates the top surface and the partial cross-sectional surface of the distal end portion in FIG. 2. FIG. 2 is a cross-sectional view that corresponds to the A-A line in FIG. 3. FIG. 4 is a diagram when the distal end portion is viewed in the direction C in FIG. 3.

As illustrated in FIG. 2, the distal end portion 2a includes a distal-end rigid portion 101 that is provided on the distal end of the distal end portion 2a; a treatment tool channel 102 that causes a treatment tool to protrude from the distal-end rigid portion 101; a raise base 103 that raises the treatment tool protruding through the treatment tool channel 102; and a rotary shaft 104 that rotatably supports the raise base 103. Furthermore, as illustrated in FIG. 3, the distal end portion 2a includes a wire 105 that is provided along the inserting direction to transmit operations, input to the operating unit 3, to the distal end portion 2a; and a seal ring 106 that is fitted onto the rotary shaft 104. Furthermore, the upper section of FIG. 3 is a diagram of part of the distal-end rigid portion 101 being removed so as to expose the top surface of the rotary shaft 104 and the wire 105, and the central section of FIG. 3 is a diagram that illustrates the cross-sectional surface that corresponds to the B-B line in FIG. 2.

The distal-end rigid portion 101 is made of a rigid material, such as resin or metal. As illustrated in FIG. 2, an opening portion 101a for protruding the treatment tool is formed in the distal-end rigid portion 101. The opening portion 101a accommodates the raise base 103 and the rotary shaft 104. Furthermore, as illustrated in FIG. 4, the distal-end rigid portion 101 is provided with an opening portion 101b for mounting the rotary shaft 104. The opening portion 101b is sealed with an undepicted cover after the rotary shaft 104 is mounted.

The treatment tool channel 102 causes the treatment tool, inserted from the treatment-tool insertion opening 3a of the operating unit 3, to protrude through the opening portion 101a of the distal-end rigid portion 101.

The raise base 103 is made of metal such as stainless steel, or an elastic material such as resin. The raise base 103 is rotated in accordance with the rotation of the rotary shaft 104 due to operation of the operating unit 3 to raise the treatment tool. The raise base 103 includes a pair of engagement sections 103a that extend in an attaching/detaching direction A1, which is a direction in which the raise base 103 is attached or detached as described later, and that are opposed to each other with the rotary shaft 104 interposed therebetween; and a pair of claw sections 103b that are provided on the distal ends of the respective engagement sections 103a and protrude toward the rotary shaft 104 from the engagement sections 103a. The claw sections 103b are engaged with the rotary shaft 104 so that the raise base 103 is prevented from being omitted from the rotary shaft 104. Furthermore, with regard to the raise base 103, the longitudinal direction of the raise base 103 is the same as the attaching/detaching direction A1, which is the direction in which the engagement section 103a extends.

The rotary shaft 104 includes a cylindrical shaft section 104a that is provided in the opening portion 101a and that extends in a vertical direction of the drawing plane of FIG. 3 (a direction perpendicular to the drawing plane of FIG. 2), which is a direction of the shaft center perpendicular to the inserting direction. The shaft section 104a rotatably supports the raise base 103 in a rotation direction A2. The shaft section 104a includes an engagement surface 104aa that extends in the attaching/detaching direction A1 and that abuts the inner surface of the engagement section 103a. Furthermore, as illustrated in FIG. 3, the rotary shaft 104 includes a wire connection section 104b that is connected to the distal end portion of the wire 105.

Here, the engagement section 103a of the raise base 103 abuts the engagement surface 104aa of the rotary shaft 104 along a direction perpendicular to the rotation direction A2 so that the raise base 103 and the rotary shaft 104 are prevented from being relatively rotated.

As illustrated in FIG. 3, the wire 105 is provided along the inserting direction and is connected to the operating unit 3 on the proximal end side so that it is movable in the inserting direction in accordance with operation of the operating unit 3. Furthermore, the wire 105 on the distal end side is connected to the wire connection section 104b of the rotary shaft 104.

The seal ring 106 is made of an elastic material such as rubber, and it is fitted into a groove formed on the rotary shaft 104. Accordingly, the wire connection section 104b of the rotary shaft 104 and the wire 105 are separated from outside so that they do not get contaminated while the endoscope 1 is in use.

Next, an explanation is given of an operation of the raise base 103 to raise the treatment tool. First, when a predetermined operation is input to the operating unit 3, the wire 105 is pulled to the proximal end side (the left side on the drawing plane of FIG. 4). When the wire 105 is moved to the proximal end side along the inserting direction, the rotary shaft 104 is rotated to the dashed-line position of FIG. 4 in a counterclockwise direction of FIG. 4 along the rotation direction A2, as illustrated in FIG. 4. Furthermore, the raise base 103 and the rotary shaft 104 are integrally rotated.

Figure 5:
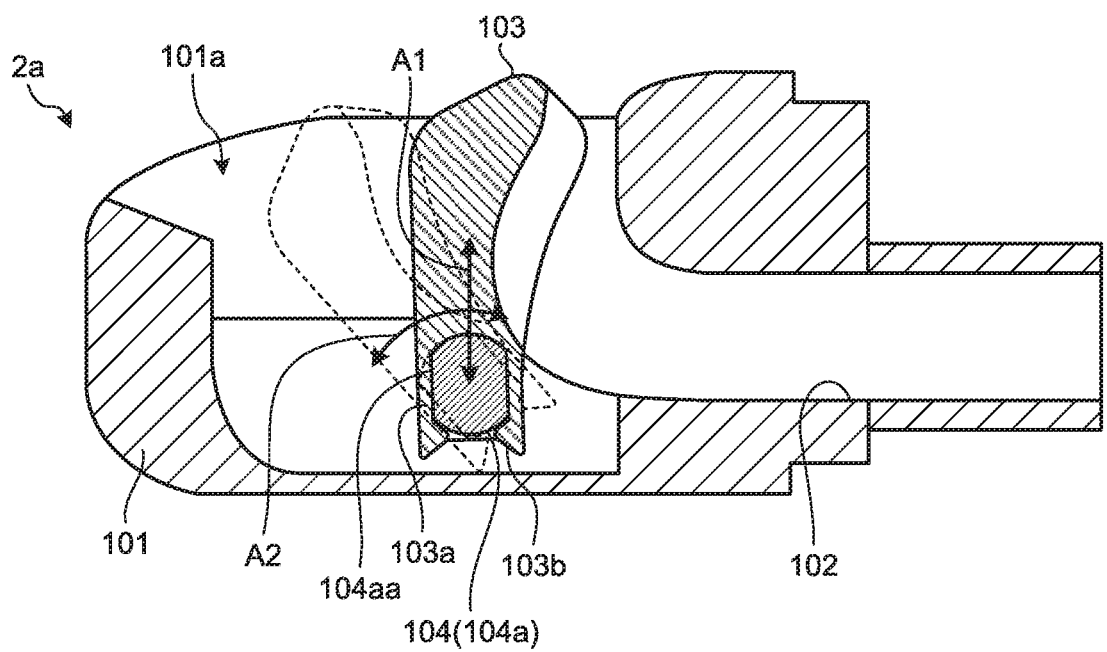
FIG. 5 is a schematic cross-sectional view that illustrates a raising state of the distal end portion in FIG. 2.

FIG. 5 is a schematic cross-sectional view that illustrates the raising state of the distal end portion in FIG. 2. The raise base 103 and the rotary shaft 104 are integrally rotated so that the raising state is obtained as illustrated in FIG. 5. Furthermore, when the raise base 103 is raised, the treatment tool abutting the raise base 103 is raised.

Next, an explanation is given of operations to attach/detach the raise base 103 to/from the rotary shaft 104.

First, an explanation is given of the operation to detach the raise base 103 from the rotary shaft 104. First of all, a user applies a force to the raise base 103 by using tweezers, or the like, to remove the raise base 103 from the rotary shaft 104. This force is applied in a direction to pull the raise base 103 along the predetermined attaching/detaching direction A1 that is perpendicular to the shaft center of the rotary shaft 104. Then, this force deforms the pair of the engagement sections 103a of the elastic raise base 103 in a direction to be separated from each other so that the engagement of the claw sections 103b with the rotary shaft 104 is eliminated. As a result, the raise base 103 is removed from the rotary shaft 104 in the attaching/detaching direction A1 through the opening portion 101a.

Next, an explanation is given of the operation to attach the raise base 103 to the rotary shaft 104. First of all, a user applies a force to the raise base 103 by using tweezers, or the like, to attach the raise base 103 to the rotary shaft 104. This force is applied in a direction to push the raise base 103 in the attaching/detaching direction A1. Then, this force deforms the pair of the engagement sections 103a in a direction to be separated from each other so that the shaft section 104a enters the interval between the engagement sections 103a in pair. Furthermore, if the shaft section 104a enters the innermost part of the engagement section 103a, the claw sections 103b are engaged with the rotary shaft 104 due to elasticity of the engagement sections 103a. As a result, the raise base 103 is prevented from being omitted from the rotary shaft 104, and the raise base 103 is attached to the rotary shaft 104 along the attaching/detaching direction A1 through the opening portion 101a.

Thus, the raise base 103 may be easily attached to or detached from the rotary shaft 104 in the predetermined attaching/detaching direction A1 through the opening portion 101*a*.

Furthermore, the endoscope 1 is configured such that the attaching/detaching direction A1 is identical to the longitudinal direction of the raise base 103. Therefore, the user may intuitively know the attaching/detaching direction A1 in performing an attaching/detaching operation. Accordingly, damages to the endoscope 1 due to the user applying a force to the raise base 103 in an improper direction are prevented.

Furthermore, the raise base 103 is made of an elastic material, and the elasticity of the engagement sections 103*a* makes it possible to be attached to/detached from the rotary shaft 104. Therefore, the raise base 103 may be configured such that at least the engagement sections 103*a* are made of an elastic material, and the entire raise base 103 may not be configured to be made of an elastic material.

As described above, the endoscope 1 according to the first embodiment makes it possible to easily attach or detach the raise base 103 through the opening portion 101*a*. As a result, the raise base 103 may be removed to be cleaned directly with a brush after the endoscope 1 is used, whereby the endoscope has a desired cleaning efficiency.

Furthermore, a configuration may be such that the raise base 103 is a disposable member and the new raise base 103 is attached after use so that the raise base 103 is kept clean.

Furthermore, when the raise base 103 is removed, the rotary shaft 104 is exposed. As illustrated in FIG. 3, the end portion of the rotary shaft 104 beyond the seal ring 106 on the shaft section 104*a* is exposed to outside, and the portion need to be cleaned. As this portion does not have a complicated structure, it is easily cleaned. Furthermore, as it is understood from FIG. 5, the endoscope 1 includes a clearance between the shaft section 104*a* and the distal-end rigid portion 101. Accordingly, the endoscope 1 may be cleaned directly by inserting a brush into the clearance, whereby the endoscope has a desired cleaning efficiency.

Figure 6:
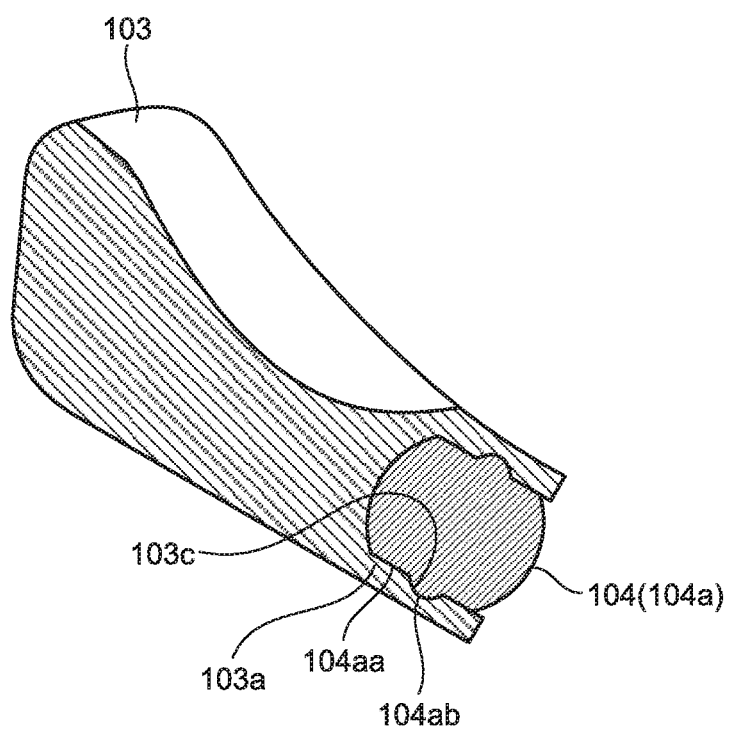
FIG. 6 is a diagram that illustrates a rotary shaft and a raise base of the endoscope according to a modification of the first embodiment.

Furthermore, the endoscope 1 according to the first embodiment is not limited to a configuration such that the claw sections 103*b* of the raise base 103 are engaged with the rotary shaft 104. FIG. 6 is a diagram that illustrates the rotary shaft and the raise base of the endoscope according to a modification of the first embodiment. As illustrated in FIG. 6, in the endoscope 1 according to the modification, the raise base 103 includes the pair of the engagement sections 103*a* that are made of an elastic material, extend in the attaching/detaching direction, and are opposed to each other with the rotary shaft 104 interposed therebetween; and recessed portions 103*c* that are provided on the inner sides with respect to a direction in which the engagement sections 103*a* are opposed to each other, and the rotary shaft 104 includes the engagement surface 104*aa* that extends in the attaching/detaching direction and that abuts the inner surface of the engagement section 103*a*; and a convex portion 104*ab* that protrudes from the engagement surface 104*aa* toward the engagement section 103*a* to be engaged with the recessed portion 103*c* of the raise base 103. Accordingly, a configuration is such that the recessed portion 103*c* of the raise base 103 is engaged with the convex portion 104*ab* of the rotary shaft 104 so that the raise base 103 is prevented from being omitted from the rotary shaft 104. In this way, there is no particular limitation on its shape as long as the endoscope 1 includes an engaging unit that prevents the raise base 103 from being omitted from the rotary shaft 104.

Second Embodiment

Next, the endoscope according to the second embodiment is explained. As the endoscope according to the second embodiment has the same configuration as that of the endoscope 1 according to the first embodiment except for the configuration of a distal end portion 22*a*, explanations are omitted as appropriate.

Figure 7:
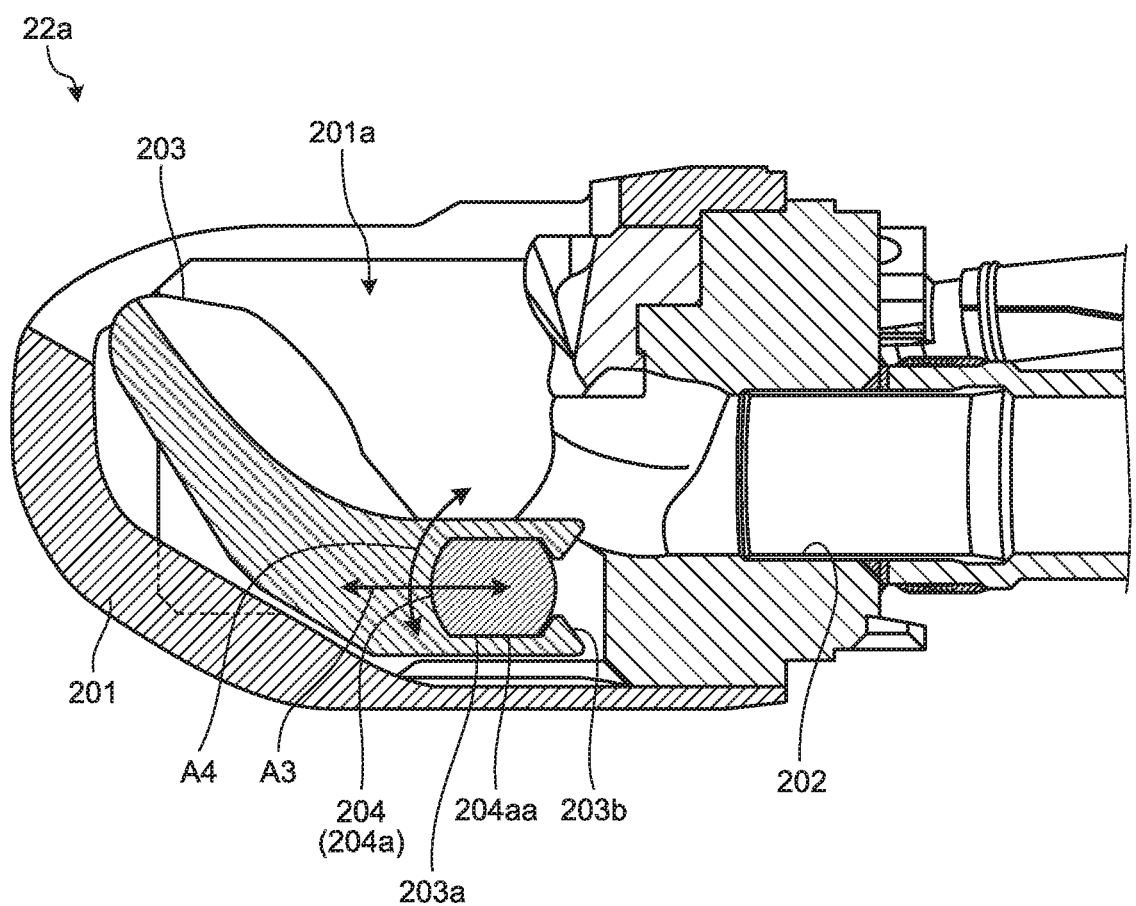
FIG. 7 is a schematic cross-sectional view of the distal end portion of the endoscope according to a second embodiment.

FIG. 7 is a schematic cross-sectional view of the distal end portion of the endoscope according to the second embodiment. As illustrated in FIG. 7, the distal end portion 22*a* of the endoscope according to the second embodiment includes a distal-end rigid portion 201 that is provided on the distal end of the distal end portion 22*a*; a treatment tool channel 202 that causes the treatment tool to protrude from the distal-end rigid portion 201; a raise base 203 that raises the treatment tool protruding through the treatment tool channel 202; and a rotary shaft 204 that rotatably supports the raise base 203.

In the distal-end rigid portion 201, an opening portion 201*a* is formed to accommodate the raise base 203.

The treatment tool channel 202 causes the treatment tool, inserted from the treatment-tool insertion opening 3*a* of the operating unit 3, to protrude through the opening portion 201*a* of the distal-end rigid portion 201.

The raise base 203 is rotated in accordance with the rotation of the rotary shaft 204 due to operation of the operating unit 3 to raise the treatment tool. The raise base 203 includes a pair of engagement sections 203*a* that extend in an attaching/detaching direction A3 and that are opposed to each other with the rotary shaft 204 interposed therebetween; and a pair of claw sections 203*b* that are provided on the distal ends of the respective engagement sections 203*a* and that protrude toward the rotary shaft 204 from the engagement sections 203*a*. Here, with regard to the raise base 203, the longitudinal direction of the raise base 203 is different from the attaching/detaching direction A3.

The rotary shaft 204 includes a cylindrical shaft section 204*a* that is provided in the opening portion 201*a* and that extends in a direction perpendicular to the drawing plane of FIG. 7, which is a direction of the shaft center perpendicular to the inserting direction, and it rotatably supports the raise base 203 in a rotation direction A4. The shaft section 204*a* includes an engagement surface 204*aa* that extends in the attaching/detaching direction A3 and that abuts the inner surface of the engagement section 203*a*. Furthermore, as is the case with the description in the first embodiment with reference to FIG. 3, the rotary shaft 204 includes the wire connection section, and it is rotated when an operation is input through the wire connection section. Furthermore, as is the case with the first embodiment, an area of the rotary shaft 204 on the side of the wire connect section is separated from outside by the seal ring so that it does not need to be cleaned.

Figure 8:
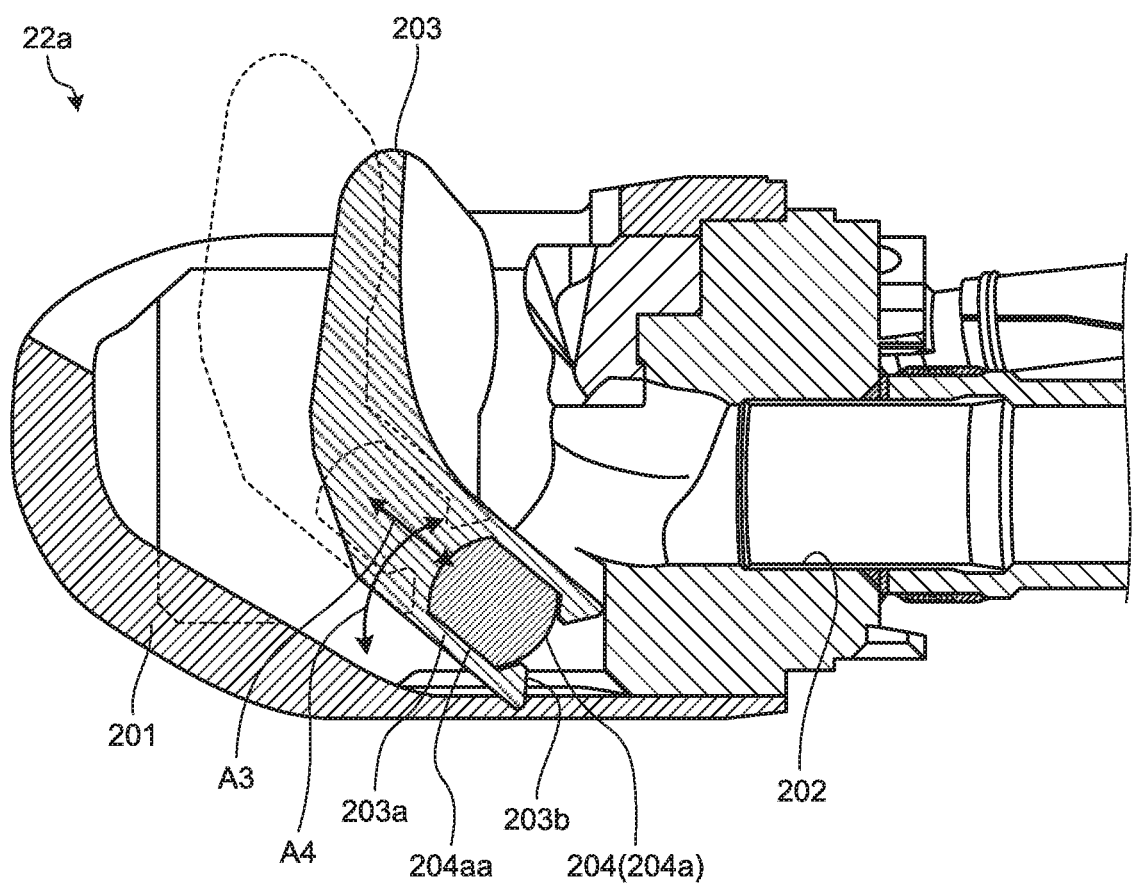
FIG. 8 is a schematic cross-sectional view that illustrates the raising state of the distal end portion in FIG. 7.

FIG. 8 is a schematic cross-sectional view that illustrates the raising state of the distal end portion in FIG. 7. As is the case with the first embodiment, in the endoscope according to the second embodiment, when a predetermined operation is input to the operating unit 3, the wire is pulled to the proximal end side so that the rotary shaft 204 and the raise base 203 are integrally rotated and the raise base 203 enters a raising state.

Furthermore, as illustrated by a dashed line in FIG. 8, in the same manner as the first embodiment, the raise base 203 may be easily attached to/detached from the rotary shaft 204 in the predetermined attaching/detaching direction A3 though the opening portion 201*a*. Accordingly, in the endoscope according to the second embodiment, the raise base 203 may be removed to be cleaned, whereby the endoscope has a desired cleaning efficiency.

Here, in the second embodiment, the longitudinal direction of the raise base 203 is different from the attaching/detaching direction A3, and the longitudinal direction of the raise base and the attaching/detaching direction do not always need to be identical.

Figure 9:
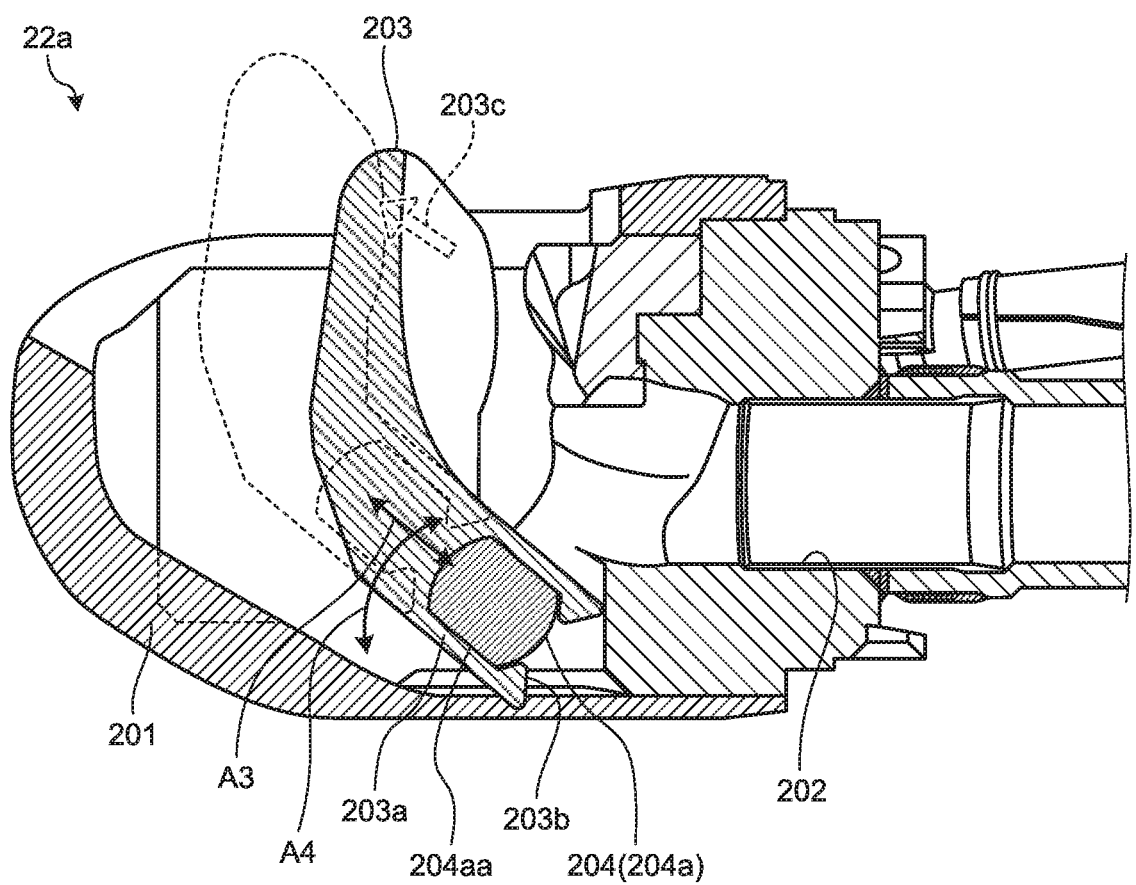
FIG. 9 is a schematic cross-sectional view of the distal end portion of the endoscope according to a modification of the second embodiment.

Furthermore, the endoscope according to the second embodiment may be configured to include an attaching/detaching-direction display unit that displays the attaching/detaching direction A3. FIG. 9 is a schematic cross-sectional view of the distal end portion of the endoscope according to a modification of the second embodiment. Here, a marker 203c as an attaching/detaching-direction display unit, indicated by a dashed line in FIG. 9, is provided by printing or forming concavity and convexity on one or both side surfaces of the raise base 203. With this endoscope, users may view the attaching/detaching direction A3. As a result, damages to the endoscope due to the user applying a force to the raise base 203 in an improper direction are prevented.

Third Embodiment

Next, an endoscope according to a third embodiment is explained. As the endoscope according to the third embodiment has the same configuration as that of the endoscope 1 according to the first embodiment except for the configuration of a distal end portion 32a, explanations are omitted as appropriate.

Figure 10:
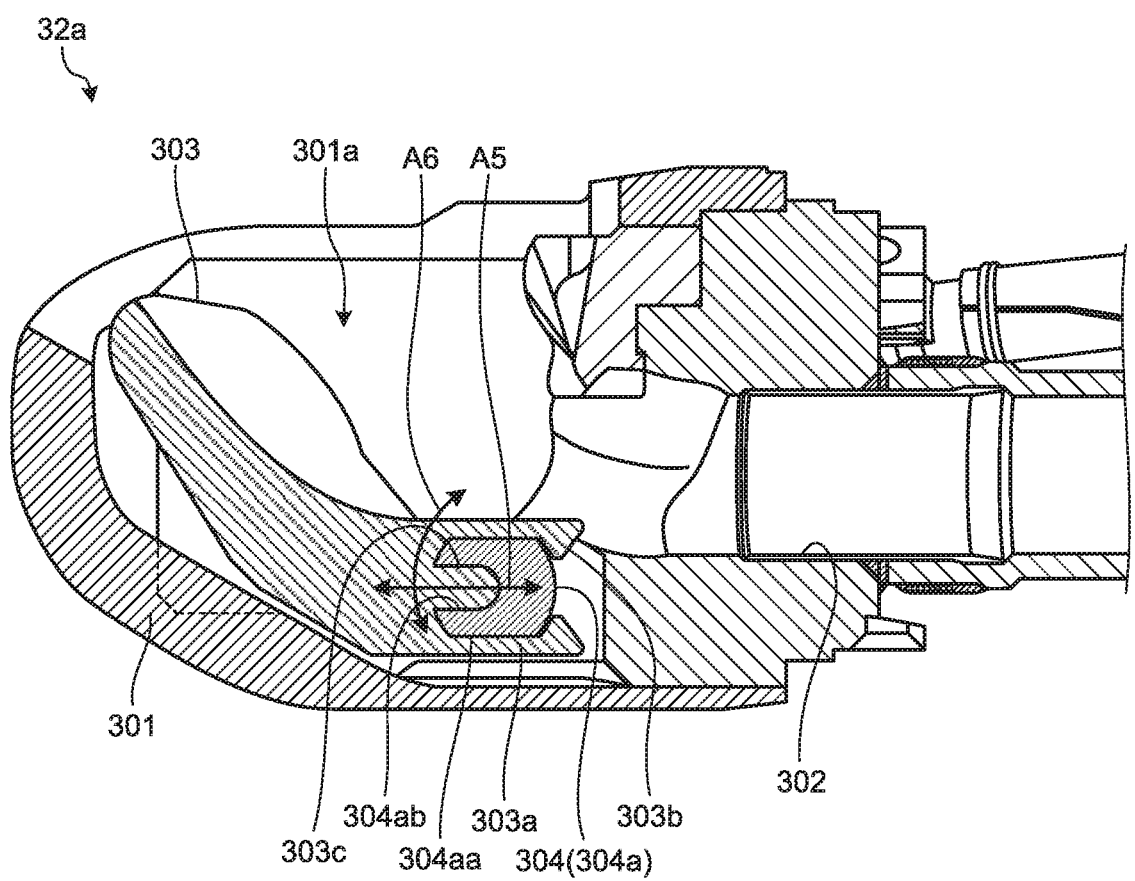
FIG. 10 is a schematic cross-sectional view of the distal end portion of the endoscope according to a third embodiment.

FIG. 10 is a schematic cross-sectional view of the distal end portion of the endoscope according to the third embodiment. As illustrated in FIG. 10, the distal end portion 32a of the endoscope according to the third embodiment includes a distal-end rigid portion 301 that is provided on the distal end of the distal end portion 32a; a treatment tool channel 302 that causes the treatment tool to protrude from the distal-end rigid portion 301; a raise base 303 that raises the treatment tool protruding through the treatment tool channel 302; and a rotary shaft 304 that rotatably supports the raise base 303.

In the distal-end rigid portion 301, an opening portion 301a is formed to accommodate the raise base 303.

The treatment tool channel 302 causes the treatment tool, inserted from the treatment-tool insertion opening 3a of the operating unit 3, to protrude through the opening portion 301a of the distal-end rigid portion 301.

The raise base 303 is rotated in accordance with the rotation of the rotary shaft 304 due to operation of the operating unit 3 to raise the treatment tool. The raise base 303 includes a pair of engagement sections 303a that extend in an attaching/detaching direction A5 and that are opposed to each other with the rotary shaft 304 interposed therebetween; and a pair of claw sections 303b that are provided on the distal ends of the respective engagement sections 303a and that protrude toward the rotary shaft 304 from the engagement sections 303a. Furthermore, the raise base 303 includes a projection section 303c that extends in the attaching/detaching direction A5 between the engagement sections 303a in pair.

The rotary shaft 304 includes a cylindrical shaft section 304a that is provided in the opening portion 301a and that extends in a direction perpendicular to the drawing plane of FIG. 10, which is a direction of the shaft center perpendicular to the inserting direction, and it rotatably supports the raise base 303 in a rotation direction A6. The shaft section 304a includes an engagement surface 304aa that extends in the attaching/detaching direction A5 and that abuts the inner surface of the engagement section 303a. Furthermore, the shaft section 304a includes a groove section 304ab into which the projection section 303c is inserted. Moreover, as is the case with the description in the first embodiment with reference to FIG. 3, the rotary shaft 304 includes the wire connection section, and it is rotated when an operation is input through the wire connection section. Furthermore, as is the case with the first embodiment, an area of the rotary shaft 304 on the side of the wire connect section is separated from outside by the seal ring so that it does not need to be cleaned.

In the endoscope according to the third embodiment, as is the case with the first embodiment, when a predetermined operation is input to the operating unit 3, the wire is pulled to the proximal end side so that the rotary shaft 304 and the raise base 303 are integrally rotated and the raise base 303 enters a raising state. Here, the projection section 303c of the raise base 303 and the groove section 304ab of the rotary shaft 304 are engaged with each other so as to function as a rotation preventing unit that prevents the raise base 303 and the rotary shaft 304 from relatively rotating. Thus, the raise base 303 is prevented from being omitted from the rotary shaft 304 due to a relative rotation of the raise base 303 and the rotary shaft 304 while the endoscope is in use.

In this way, the endoscope may be configured to include the rotation preventing unit that prevents the raise base 303 and the rotary shaft 304 from relatively rotating. The rotation preventing unit may be not only a projection section and a groove section but also for example a rod and a hole or concavity and convexity that are engaged with each other. Furthermore, a configuration may be such that the raise base 303 includes a groove section and the rotary shaft 304 includes a projection section.

Furthermore, as is the case with the first embodiment, the raise base 303 may be easily attached to/detached from the rotary shaft 304 in the predetermined attaching/detaching direction A5 through the opening portion 301a. As a result, in the endoscope according to the third embodiment, the raise base 303 may be removed to be cleaned, whereby the endoscope has a desired cleaning efficiency.

Furthermore, the configuration according to the above-described embodiment may be adapted to an ultrasound endoscope that includes an ultrasound transducer provided on the distal end of an insertion section. In the ultrasound endoscope, the transducer is provided on the distal end, and the cable connected to the transducer is passed through under the opening portion of the distal-end rigid section. For this reason, it is difficult to ensure water-tightness of the distal end portion including the transducer while the configuration enables decomposition for cleaning. Furthermore, in order to obtain such a configuration, the size of the distal end portion sometimes becomes larger. Therefore, the configuration according to the above-described embodiment is also applied to ultrasound endoscopes so that the raise base may be removed to be cleaned without decomposing the distal end portion, whereby an ultrasound endoscope with a desired cleaning efficiency may be achieved.

Furthermore, the present disclosure is not limited to the above-described embodiments. The present disclosure also includes the configuration that combines the above-described components as appropriate. Moreover, further advantages and modifications may be easily derived by a person skilled in the art. Thus, a wider range of scope of the present disclosure is not limited to the above-described embodiments, and various changes may be made.

According to the present disclosure, an endoscope with a desired cleaning efficiency may be achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope adapted to insert a treatment tool, the endoscope comprising:
   an opening from which the treatment tool protrudes, the opening being provided on a distal end of the endoscope;
   a rotary shaft rotatably mounted in the opening, a direction of a shaft center of the rotary shaft being perpendicular to a longitudinal direction of the endo scope; and
   a raise base that is attachable to the rotary shaft and detachable from the rotary shaft in a predetermined attaching/detaching direction through the opening, the raise base being configured to rise around the rotary shaft while being attached to the rotary shaft, wherein
   the raise base includes a pair of engagement sections made of an elastic material, the pair of engagement sections extending in the attaching/detaching direction and opposing to each other with the rotary shaft interposed therebetween,
   the rotary shaft includes an engagement surface extending in the attaching/detaching direction and abutting an inner surface of the engagement section, and
   one of the pair of engagement sections and the rotary shaft further comprising a projection configured to project toward a direction intersecting with the attaching/detaching direction.

2. The endoscope according to claim 1, further comprising:
   an operating unit configured to receive an operation for rotating the rotary shaft; and
   a wire provided along the longitudinal direction, the wire having a proximal end connected to the operation unit, the wire having a distal end connected to the rotary shaft,
   wherein the rotary shaft includes a shaft section that is perpendicular to the longitudinal direction, and a wire connection section connected to the distal end of the wire, and
   the operating unit raises the treatment tool by raising the raise base by rotating the shaft section of the rotary shaft by using the wire in accordance with the operation.

3. The endoscope according to claim 1, wherein
   the projection is provided on distal ends of the respective engagement sections to protrude from the engagement sections toward the rotary shaft.

4. The endoscope according to claim 3, wherein a longitudinal direction of the raise base is identical to a direction in which the engagement section extends.

5. The endoscope according to claim 1, wherein
   the raise base includes
   a recessed portion provided on an inner side with respect to a direction in which the engagement sections are opposed to each other, and
   the projection is a convex portion protruding from the engagement surface toward the engagement section to be engaged with the recessed portion of the raise base.

6. The endoscope according to claim 1, wherein the raise base includes an attaching/detaching-direction display marker configured to indicate the attaching/detaching direction.

7. The endoscope according to claim 1, further comprising a rotation preventing unit configured to prevent the raise base and the rotary shaft from relatively rotating.

8. The endoscope according to claim 7, wherein the rotation preventing unit includes
   a groove formed on one of the raise base and the rotary shaft; and
   a projection formed on an other of the raise base and the rotary shaft.

9. The endoscope according to claim 1, wherein the endoscope is an ultrasound endoscope that further includes an ultrasound transducer provided on a distal end.

10. The endoscope according to claim 1, further comprising an elastic member provided around the rotary shaft in a middle of an axial direction of the rotary shaft such that the elastic member contacts a circumference surface of the rotary shaft.

* * * * *